(12) United States Patent
Willard et al.

(10) Patent No.: US 6,884,763 B2
(45) Date of Patent: Apr. 26, 2005

(54) WATERLESS HAND CLEANER CONTAINING PLANT DERIVED NATURAL ESSENTIAL OIL

(75) Inventors: Dean M Willard, New York, NY (US); George Barraza, Avon, CT (US); Jonathan D. Zook, Santa Clarita, CA (US)

(73) Assignee: Permatex, Inc., Solon, OH (US)

( * ) Notice: Subject to any disclaimer, the term of this patent is extended or adjusted under 35 U.S.C. 154(b) by 0 days.

(21) Appl. No.: 10/282,634

(22) Filed: Oct. 29, 2002

(65) Prior Publication Data

US 2003/0083212 A1 May 1, 2003

Related U.S. Application Data

(60) Provisional application No. 60/340,893, filed on Oct. 30, 2001.

(51) Int. Cl.$^7$ ................................................ A61K 7/02
(52) U.S. Cl. .................. 510/136; 156/463; 156/424; 442/60; 424/402
(58) Field of Search ................. 510/424, 130, 510/136, 156, 463; 424/402; 442/60

(56) References Cited

U.S. PATENT DOCUMENTS

| | | | |
|---|---|---|---|
| 4,251,383 A | 2/1981 | Kemp | 252/118 |
| 4,313,847 A | 2/1982 | Chasin et al. | 252/356 |
| 4,380,506 A | 4/1983 | Kimura et al. | 252/398 |
| 4,421,769 A | 12/1983 | Dixon et al. | 424/358 |
| 4,828,750 A | 5/1989 | Simion et al. | 252/142 |
| 4,900,721 A * | 2/1990 | Bansemir et al. | 514/25 |
| 5,259,984 A * | 11/1993 | Hull | 510/138 |
| 5,416,075 A | 5/1995 | Carson et al. | 514/23 |
| 5,480,633 A | 1/1996 | Simion et al. | 424/70.1 |
| 5,646,104 A | 7/1997 | Erilli et al. | 510/365 |
| 5,683,971 A | 11/1997 | Rose et al. | 510/130 |
| 5,874,393 A | 2/1999 | Drapier et al. | 510/417 |
| 5,910,455 A * | 6/1999 | Maddern et al. | 442/60 |
| 5,955,086 A | 9/1999 | DeLuca et al. | 424/195.1 |
| 6,008,180 A | 12/1999 | Drapier et al. | 510/417 |
| 6,010,991 A * | 1/2000 | Dabestani | 510/139 |
| 6,048,834 A | 4/2000 | Drapier et al. | 510/417 |
| 6,048,836 A | 4/2000 | Romano et al. | 510/490 |
| 6,114,298 A | 9/2000 | Petri et al. | 510/372 |
| 6,121,228 A | 9/2000 | Drapier et al. | 510/417 |
| 6,287,583 B1 | 9/2001 | Warren et al. | 424/404 |
| 6,319,887 B1 | 11/2001 | Mertens | 510/417 |
| 6,333,301 B1 | 12/2001 | Kamiya | 510/438 |
| 6,342,475 B1 | 1/2002 | Durbut et al. | 510/426 |
| 6,346,281 B1 | 2/2002 | DeAth et al. | 424/725 |
| 6,369,013 B1 | 4/2002 | Gambogi et al. | 510/237 |
| 6,372,710 B2 | 4/2002 | Sadoyama | 510/531 |
| 6,387,866 B1 | 5/2002 | Mondin et al. | 510/384 |
| 6,432,429 B1 * | 8/2002 | Maddern et al. | 424/402 |
| 6,583,097 B2 * | 6/2003 | McDonald | 510/365 |
| 2002/0002124 A1 * | 1/2002 | Biedermann et al. | 510/218 |

FOREIGN PATENT DOCUMENTS

| | | |
|---|---|---|
| JP | 357056416 A | 4/1982 |
| JP | 407267873 A | 10/1995 |

OTHER PUBLICATIONS

Enviro$en$e "Fact Sheet: Aqueous Cleaner Additives For Industrial Cleaning" Oct. 17, 1995.
Uncle Harry's Natural Products "Oregano Oil—The Most Powerful Plant–Derived Antiseptic" from www.uncleharrys.com.
"Wild Oregano: a Potent Natural Antibiotic" from kitchendoctor.com.
Anne Lee's Oregano Soap from annelees.com.
Rahelica olive oil soaps.
Articles: Gogoi "Seeking an Anthrax Cure in Your Spice Garden" Business Week Magazine Oct. 22, 2001; "Oregano, Other Essential Oils Destroy Strep Pneumonia Cells" Optimal Wellness Health News Jun. 1, 1998; "Ailment—Anthrax" Gateway to Wellness website; Susman "Oregano Oil, Garlic Aren't Anthrax Fighers" Cox News Service Oct. 17, 2001.
Exxon Chemical, "Starting Formulas—LVP Solvents for Consumer Products: Household, Automotive and Insecticide Applications": Hard Cream Paste Auto Polish; Tomah Products, Inc. Hand Cleaners; AG Environmental Products L.L.C. Waterless Hand Cleaner; Hand cleanser—clear gel with solvent & Hand cleanser with abrasive; Shell Chemical Company Technical Bulletin SC:1–74 "Waterless Handcleaners".

\* cited by examiner

Primary Examiner—Necholus Ogden
(74) Attorney, Agent, or Firm—Gifford, Krass, Groh, Sprinkle, Anderson & Citkowski, P.C.

(57) ABSTRACT

A waterless hand cleaner formulation includes an organic solvent, a quantity of water and a surfactant present to form a gelatinous emulsion. The gelatinous emulsion is loaded with 0.1 to 25 total weight percent of a natural essential oil having topical antimicrobial activity. Oil of oregano is particularly well suited for this application.

22 Claims, No Drawings

WATERLESS HAND CLEANER CONTAINING PLANT DERIVED NATURAL ESSENTIAL OIL

RELATED APPLICATION

This application claims priority of U.S. Provisional Patent Application No. 60/340,893 filed Oct. 30, 2001, which is incorporated herein by reference.

FIELD OF THE INVENTION

The present invention generally relates to hand cleaner formulations containing "plant derived" antimicrobial cleansing compositions. Specifically, the inventive composition provides residual antimicrobial activity.

BACKGROUND OF THE INVENTION

Industrial and hand cleansing formulations typically contain a surfactant that solubilizes or emulsifies the oils, debris, and soil present on a substrate. These formulations inherently have oil-cleansing limitations when oil-emulsifiability or solvency alone is used as a cleaning mechanism. When only surfactants in combination with non-aggressive solvent cleansers are used in the cleansing compositions, the cleaning power of the composition may be inadequate when stubborn or embedded oils are present. If the chemical formula is too aggressive in terms of its solubilizing or emulsifying power, skin can be harmed due to defatting of the dermal oils thereof, particularly when the cleanser is used repeatedly.

Many cleansing formulations that are currently available in the marketplace also contain abrasive particulates that mildly scour the skin surface to aid in the removal of embedded oils, debris and soil. Some examples of the abrasive particulates utilized are pumice, silica, and diatomaceous earth. These formulations can be of a "waterless" nature, a term indicating that water does not have to be added during the hand cleansing process. However, because this abrasive particulate is generally insoluble, it must be flushed away with water after the cleansing process to achieve residue-free hands, i.e., free of the fine abrasive particulate that would remain on the skin if not rinsed away.

After cleansing and rinsing, hands are often dried with a towel or cloth instead of air drying for purposes such as speed and convenience, as well as to aid in mechanically removing any stubborn soils that remain on the skin.

Nonabrasive waterless hand cleansers that are currently commercially available have a gelatinous or paste-like high viscosity consistency. These cleansers often have both polar and nonpolar ingredients that are blended together to achieve removal of a wide variety of soils from the surface of the skin. The gelatinous surfactant that affords this type of waterless cleanser its gelatinous form also acts as a substrate to essentially permanently bind the emulsion of cleansing ingredients together. This gelatinous consistency has been essential for waterless hand cleansers in order for them to achieve the continuous cleansing action necessary for the desired cleaning effectiveness due to extended contact between the cleanser and the skin, as the user can work and rework the cleanser on the skin in order to fully solubilize the oils and debris until they are removed from the skin surface. If the cleanser were liquid instead of gelatinous, the necessary continuous cleansing action associated with waterless hand cleansers would not be achieved because the extended contact between the cleanser and the skin is not achieved. The lower viscosity of a liquid cleanser can also cause the cleanser to run off of the hands, thereby facilitating the potential waste of cleanser. Thus, the gelatinous or high viscosity nature of waterless hand cleansers has several advantages in comparison to liquid cleansers. Additionally, these hand cleanser formulations typically contain one or more antibacterial compounds. These compounds simultaneously provide in-package resistance to bacterial buildup and a degree of hand "sanitization" when they are used.

Human health is impacted by many microbial entities. Inoculation by viruses and bacteria cause a wide variety of sicknesses and ailments. Topical antimicrobial infections are well known causes of food poisoning, dysentery, and other serious illnesses.

It is well known that the washing of hard surfaces, food (e.g. fruit or vegetables) and skin, especially the hands, with antimicrobial or non-medicated soap, can remove many viruses and bacteria from the washed surfaces. Removal of the viruses and bacteria is due to the surfactancy of the soap and the mechanical action of the wash procedure. Therefore, it is known and recommended that people wash frequently to reduce the spread of viruses and bacteria.

Antibacterial cleansing products have been marketed in a variety of forms for some time. Forms include antibacterial soaps, hard surface cleaners, and surgical disinfectants. Rinse-off antimicrobial soaps have been formulated to provide bacteria removal during washing. Such conventional antibacterial cleansing products have been shown to also provide a residual effectiveness against some common gram-positive bacteria. Antimicrobial active agents are deposited on the washed surface during the washing process. The residual active ingredient controls the viability and growth of some surviving and some newly contacted transient bacteria. For example, antibacterial soap, when used regularly in hand washing, has been found to provide a 90% to 97% reduction in gram-positive bacteria after two to five hours. Unfortunately, there are concerns that typical topical antibacterial agents such as pyrithiones, thiazolones, sulfites, diazo compounds, chlorinated organics, brominated organics, phenols, bisphenols, resourcinols, and alkylated parabens lead to antibiotic resistance.

Antimicrobial liquid cleansers are disclosed in U.S. Pat. No. 4,847,072, Bissett et al., issued Jul. 11, 1989; U.S. Pat. No. 4,939,284, Degenhardt, issued Jul. 3, 1990; and U.S. Pat. No. 4,820,698, Degenhardt, issued Apr. 11, 1989, all patents being incorporated herein by reference.

Wild oregano is an oil rich plant. Each oregano leaf contains hundreds of oil glands. Oil of oregano is rich in a variety of natural compounds. The primary constituent of this oil is polyphenolic flavonoids. Of these, carvacrol and thymol are potent natural antiseptics. In fact carvacol and thymol work together with synergistic effect. The efficacy of carvacol and thymol in natural oil is more potent than synthetic types—probably due to the fact that synthesis so far has been unable to exactly recreate carvacol. Although the antimicrobial activity of carvacol and thymol is known and are the primary active ingredients, natural oil of oregano contains more than thirty compounds and synthetic reproduction of all these active compounds is problematic.

The following list details known compounds found in oil of oregano:

| | | |
|---|---|---|
| alpha-pinene | linalyl acetate | Camphene |
| Beta-bisabolene | 6-methyl-3-heptanol | carvacrol |

-continued

| | | |
|---|---|---|
| calemene | p-cimene-8-ol | beta-caryophyllene |
| cineole | phellandrene | cis-dihydrocarvone |
| cis-sabinene hydrate | sabinene | cymene |
| decane | gamma-terpinene | germacrene D |
| carvacrol acetate | terpinolene | hexanal |
| limonene | trans-dihydrocarvone | linalool |
| methylcarvacrol | p-cimene | Myrcene |
| beta-pinene | Spartholerol | terpinen-4-ol |
| Thymol | Undecane | |

Oregano oil has been tested against a variety of microorganisms and is found to exert a high degree of anti-fungal, anti-parasitic, anti-viral and antibacterial actions. In addition to containing essential oils, oregano is a rich source of a variety of vitamins and minerals, and is especially rich in vitamin C. Oregano contains large amounts of chlorophyll, itself a natural antiseptic. Numerous research reports prove that oregano is highly effective for killing a wide range of fungi, yeast and bacteria as well as parasites and viruses.

Oil of oregano is a natural antiseptic that possesses a wide range of microbial killing powers. Unlike synthetic antibiotics there is no known tendency for development of microbial resistance to oil of oregano. Oil of oregano has demonstrated ability to kill or inhibit growth of virtually any fungus as well as inhibiting growth of many pathogenic bacteria.

While some natural plant oils have been known since antiquity to have curative properties, the topical and oral benefits of natural plant oils has more recently been attributed to antimicrobial properties. Of the natural essential oils, oregano oil has been used as a reference for the comparison of the bactericidal action of other substances owing to its near ideal antibacterial properties. P. Belaiche, "Traité de Phylothérapie et d'aromathérapie", Vol. 1 S. A. Maloine, editor, 1979. In the case of wild oregano oil, one part per 4,000 is sufficient to sterilize contaminated water and owing to the complex mixture of antimicrobial compounds found therein, the evolution of organism resistance is considered far less likely than with single compound synthetic antimicrobials. Perhaps owing to the ill defined composition of natural essential plant oils, these oils have failed to find their way into industrial cleaning solutions and gels. Thus, there exists a need for an industrial cleaning formulation containing a broad antimicrobial spectrum natural essential plant oil.

SUMMARY OF THE INVENTION

A waterless hand cleaner formulation includes an organic solvent that is compatible with skin, and a quantity of water. A surfactant mixed with the organic solvent and the quantity of water forms a gelatinous emulsion therebetween. The gelatinous emulsion contains 0.01 to 25 total weight percent of the natural essential oil having topical antimicrobial activity. The addition of a natural essential oil having topical antimicrobial activity to a waterless hand cleaner formation represents an improvement of the prior art in maintaining a conventional waterless hand cleaner stability and properties, while enhancing antimicrobial properties with diminished concern about microbial evolutionary resistance occurring. A process for cleaning and sanitizing a skin surface is also detailed. The process includes the application to a skin surface of a waterless hand cleaner containing from 0.01 to 25 total weight percent of a natural essential oil having antimicrobial activity. After allowing sufficient contact time between the hand cleaner and the skin surface, a cleaned skin surface results. Typically, thirty seconds to three minutes is sufficient to clean and sanitize the skin surface. Thereafter, the excess hand cleaner is removed from the now cleaned and sanitized skin surface by wiping or water rinsing.

DETAILED DESCRIPTION OF THE PREFERRED EMBODIMENTS

The present invention has utility as a waterless hand cleaner. The invention is derived from the novel appreciation that natural essential oils afford superior antimicrobial performance to an otherwise conventional waterless hand cleaner composition while still maintaining the gelatinous stabilized consistency required of a waterless hand cleaner formulation. The gelled viscosity of an inventive waterless hand cleaner formulation is necessary to provide sufficient skin surface residence time for satisfactory soil and grease removal to occur.

Antibacterial agents that are useful in the present invention are the so-called "natural" antimicrobial actives, referred to as natural essential oils. These actives derive their names from their natural occurrence in plants. Natural essential oil antimicrobial actives according to the present invention include oils of anise, lemon, orange, oregano, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradensis, Berberidaceae daceae, Ratanhiae* and *Curcuma longa*. Also included in this class of natural essential oils are the key chemical components of the plant oils that have been found to provide the antimicrobial benefit. These chemicals include, but are not limited to anethol, catechol, camphene, carvacrol, eugenol, eucalyptol, ferulic acid, famesol, hinokitiol, tropolone, limonene, menthol, methyl salicylate, thymol, terpinol, verbenone, berberine, ratanhiae extract, caryophellene oxide, citronellic acid, curcumin, nerolidol and geraniol. A natural essential oil is active in quantities from 0.01 to about 25 weight percent. Preferably, a natural oil is present from 0.1 to 3 total weight percent. More preferably, a natural oil is present from 0.3 to 1 total weight percent.

As used herein, the term "antimicrobial activity" is defined to include an inhibition zone of at least two millimeters around a colony of pathogenic or potentially pathogenic skin colonizing gram-positive, gram-negative or fungal organisms on an agar plate where a test substance is applied to a planar colony at a concentration of 0.5 microliters per square centimeter of organism growth medium surface area, following 24 hours of incubation.

As used herein, a "waterless hand cleaner" is defined to include a composition that removes soil and/or grease from a skin surface absent the addition of water during the hand cleansing process even though water is optionally used thereafter as a rinsing agent.

In a preferred embodiment, the natural essential oil is the complex mixture of substances making up oregano oil. While it is appreciated that this and other natural oils vary in the amount and ratio of constituent components illustratively based on plant variety, growing conditions, plant portions harvested for extraction, and extraction process, these natural oils are nonetheless operative. With varying amounts of such natural oils being needed as an active ingredient based on antimicrobial activity.

It is appreciated that the active natural essential oil component of an inventive topical antimicrobial is formulated into a variety of conventional waterless hand cleaner formulations. These formulations illustratively including lipophilic solvents such as mineral spirits, $C_1$–$C_{30}$ oils, $C_1$–$C_{30}$ alcohols, $C_1$–$C_{30}$ fatty acids, and terpenoids; emollients such as lanolin, surfactants and detergents; fragrances; perfumes; thixotropic agents, water; chelating agents such as EDTA; bases such as caustic soda; antioxidants such as tocopherol acetate, ascorbate and BHT; thickeners such as propylene glycol; film forming plant extracts such as aloe vera; cellulosic material; starch; preservatives; and inorganic fillers and antimicrobials such as ZnO.

An inventive waterless hand cleaner formulation contains an emulsifiable organic solvent that is compatible with human skin contact. The emulsifiable organic solvent is present from 2 to 70 total weight percent and is capable of solubilizing lipophilic greases and soils. An organic solvent operative herein includes straight chain or branched chain aliphatic hydrocarbons having from about 6 to about 24 carbon atoms, alkaline glycol, alkaline glycol ether, dibasic ester, and alkyl-substituted aromatics. Specific examples of operative organic solvents illustratively include kerosene, naphtha, petroleum distillate, toluene, d-limonene, phenoxy ethanol, octanol, methyl soyate, cetyl acetate, and acetylated lanolin alcohol.

A surfactant is also present in an inventive waterless hand cleaner formulation to form an emulsion between the emulsifiable organic solvent and water also present in the formulation. A surfactant operative herein is a water soluble or water dispersible nonionic, anionic, cationic, or an amphoteric compound with emulsifying abilities. A surfactant operative herein is any conventional surfactant known to the art. A representative listing of surfactants and properties thereof is detailed in Remington's Pharmaceutical Sciences, $17^{th}$ edition (Mack Publishing Company). The hydrophilic lipophilic balance (HLB) value of an inventive formulation independent of the natural essential oil is dictated by the desired balance between degreasing properties and aqueous washability. The choice of surfactant, while largely dictated by these requirements, is also selected so as to afford a stable gelatinous state in the presence of a given concentration of natural essential oil. It is appreciated that a second surfactant is often helpful in adjusting the inventive composition HLB value, especially when the given natural essential oil induces a modification thereof. It is further appreciated that the second surfactant is independently a nonionic, anionic, cationic, or amphoteric emulsifying compound.

Amine soaps, namely $C_8$–$C_{60}$ fatty acids and fatty amines, are exemplary of operative surfactants. Alkano amines are well known to neutralize fatty acids in oily components thereby creating surfactant amine soaps. The choice of a single amine or dual amine system is well known in the art of formulating waterless hand cleaners. A dual amine soap surfactant system is known to afford good degreasing and water rinsibility properties. Representative fatty acid surfactants illustratively include oleic, stearic, palmitic, myristic and coconut. The choice of a particular fatty acid is dictated by dissolution properties with regard to heating, above ambient room temperature being necessary for dissolution, resulting gel stiffness, evaporative losses impacting shelf and stress stability, and the necessity for using in conjunction with a superior surfactancy compound. It is well known that coconut and myristic acids are used in conjunction with a superior surfactancy fatty acid.

Representative amine soaps include those derived from mono-, di- and tri-alkyl amines where the alkyl groups are each $C_1$–$C_8$ containing groups, such as methyl, ethyl, butyl and hexyl amines. Triethanol amine (TEA) soaps are particularly preferred. Specific examples of operative amine soaps operative herein include TEA-stearate, TEA-oleate and TEA soyate.

Nonionic surfactants operative herein representatively include condensation products of an organic, aliphatic or alkyl aromatic hydrophobic compound and ethylene oxide; or alternatively, the hydrophobic compound is condensed with a polyalkylene glycol. It is appreciated that the relative ratio of ethylene oxide or polyethylene glycol to hydrophobic organic, aliphatic or alkyl aromatic is adjustable to modify the HLB value of the resulting emulsifier.

Nonionic surfactants having condensation products of aliphatic substituted phenols having aliphatic substituents including from 6–24 carbon atoms and straight or branched chain configurations are well known. The aliphatic substituted phenols condensed with 1–10 moles of ethylene oxide. Preferably, 2–6 moles of ethylene oxide. Specific preferred compounds include n-molar ethoxylated nonylphenol also denoted a nonoxynol-n where n is a rational number between 2.5 and 15. Such nonionic emulsifiers are available from Huntsman Chemical (Salt Lake City, Utah).

Another suitable class of nonionic surfactants includes ethoxylated aliphatic alcohols where the base alcohol contains from 6–24 carbon atoms in straight or branched chain configuration. Typically 2–24 moles of ethylene oxide is condensed with the base alcohol. Preferably, 4–8 moles of ethylene oxide is condensed with the base alcohol to form the alkanol ethoxylate. It is appreciated that suitable nonionic surfactants are also prepared with the substitution of propylene oxide for some or all of the ethylene oxide in the condensation with aliphatic alcohols or alkyl aromatics as detailed herein. Still other derivatives of aliphatics containing 6–24 carbon atoms combined through a sulfur linkage to aliphatic, polyalkene glycol, or alkyl substituted aromatic groups are thioether; glyceride esters that are aliphatic, polyalkene glycol or alkyl substituted aromatic derivatives of glycerides; and ethoxylated alkyl mercaptans where the base thiol contains from 6–24 carbon atoms in straight or branched configuration with 4–24 moles of ethylene oxide; and mono- and di-$C_2$ or $C_3$ alcohol amides illustratively including acetamide-, cocamide-, lauramide-, lactamide-, oleamide-, palm kernel amide-, stearamide-, isostearamide-, soyamide-, tallamide-, mono- or di-alkyl amines.

Generally, a lower ratio of ethoxylation to base compound results in a formulation more likely to yield a stiff gel with better high temperature stability. In contrast, a higher ethoxylation to base compound ratio of generally greater than 7:1 tends to afford water solubility and therefore give better water rinsibility properties.

Water represents an essential component of an inventive waterless hand clear and is typically present from 5 to 70 total weight percent. In preparing an inventive formulation, an oil phase containing organic solvent and other lipophilic components is mixed with a water phase. It is appreciated that the dissolution of the surfactant and the natural essential oil in either the oil phase or water phase is known to one skilled in the art based upon the specific identities thereof. While natural essential oils are almost always dissolved in an oil phase, the segregation of the surfactant prior to homogenization between the oil phase and water phase is identity specific. For instance, while fatty acids and low ethoxylation ratio nonionic surfactants are typically dissolved in an oil phase, amine soaps and high ethoxylation ratio nonionic surfactants are typically segregated in the water phase. Typically, the two phases are combined with heating to from 60° to 90° Celsius with constant stirring until a homogeneous smooth gel forms.

The natural essential oils according to the present invention are chosen for their antimicrobial activity and the inability of microbes to develop resistance thereto. While purified active compounds within a natural oil are recognized to be operative herein, it is preferred that a natural essential oil be used in impure form and therefore containing a complex solution of compounds varying in individual antimicrobial activity. As the mechanism of antimicrobial activity is most often unknown for natural essential oils, additional refining beyond the oil state is anticipated to modify the antimicrobial activity in a negative fashion and possibly promote microbe evolutionary resistance. However, in the case of a defined antimicrobial in a natural oil such as carvacrol and carvacrol derivatives in oil of oregano, oil of oregano having at least 60% carvacrol and carvacrol derivatives assures a base level of antimicrobial activity. Most samples of oregano oil met this base level. Oil of oregano is optionally enriched to at-least 80% by total weight carvacrol and carvacrol derivatives to enhance residual antimicrobial activity. A carvacrol enriched oregano oil is appreciated to be operative at a lower total natural oil loading and still maintain antimicrobial properties following cleaning composition rinse off. Owing to the complex mixture of compounds associated with the natural oil, and the lipophilic nature of such an oil, compensating changes in the base waterless hand cleaner formulation optionally include decreasing the amount of organic solvent commensurate with the amount of natural essential oil, increasing the amount of surfactant by 0.01 to 0.5 times the weight percentage of natural essential oil, and the addition of a thickener such as hydroxy alkyl cellulose in order to modify topical diffusion of the natural essential oil.

Optionally, a stabilizer is provided in order to improve shelf and stress stability and modify gel viscosity. A stabilizer according to the present invention includes any conventional stabilizer and specifically includes polymeric thickeners, hydrogenated vegetable oils, or an inorganic particulate dispersant. A polymeric thickener operative herein illustratively includes guar gums; anionic, nonionic, cationic and lipophilicly modified guar gums having a molecular weight of 1,000–1,000,000; polyacrylic acids, methacrylic acids, cellulose resins, polyethylene glycols, hydroxy alkyl celluloses, carboxy alkyl celluloses, polyalkylene amines, such as polyethylene amine, starches, modified starches; salts thereof; and combinations thereof each having molecular weights ranging from about 1,000 to 4,000,000. A hydrogenated vegetable oil operative herein illustratively includes hydrogenated castor-oil and hydrogenated soybean oil. Inorganic particulate dispersant operative herein includes fumed silica having an average particle size of 0.01–10 microns, fumed silica having a surface area of greater than 25 meter squared per gram; clays such as bentonite, hectorite and smectite and is present from 0.001 to 10 total weight percent. Preferably, the stabilizer is present from 0.1 to 3 weight percent.

An emollient is optionally added advantageously. Compounds operative herein as emollients illustratively include propylene glycol, glycerin and lanolin. An emollient, when present, is typically present from 1 to 20 total weight percent. Preferably, an emollient, when present, accounts for from 3 to 12 total weight percent. Optionally, a thixotropic is also present in a formulation according to the present invention. A thixotropic according to the present invention illustratively includes a clay such as montmorillonite, attapulgite or kaolinite clay. The thixotropic agent when present typically accounts for up to 10 total weight percent. Preferably, the thixotropic agent is present from 0.1 to 2 total weight percent.

A formulation according to the present invention optionally includes a wide range of additional ingredients. The CTFA International Cosmetic Ingredient Dictionary, 6$^{th}$ Edition, 1995 details a wide variety of nonlimiting cosmetic ingredients commonly found in skincare products which are suitable for use herein. These additional ingredients include broad classes of compounds including: abrasives, antioxidants, chelating agents, colorants, astringents, fragrances, preservatives, pH adjusting agents and sunscreen.

EXAMPLES

The following examples are given for the purpose of illustration and are not to be construed as a limitation on the present invention, since numerous variations of the practice thereof are possible without departing from the spirit and scope of the invention as claimed. The following hand cleaner formulations are provided in total weight percent unless otherwise noted.

An exemplary inventive hand cleaner formulation includes:

| Component | wt % |
| --- | --- |
| Lipophilic Organic Solvent | 2–70 |
| Surfactant | 0.5–40 |
| Emollient | 0–20 |
| Fragrance | 0–5 |
| Thixotropic Agent | 0–10 |
| Water | 5–70 |
| Chelating Agent | 0–20 |
| Antioxidant | 0–20 |
| Stabilizing Thickener | 0–10 |
| Preservative | 0–10 |
| Active Natural Essential Oil | 0.01–25 |

A specific exemplary inventive formulation includes:

| Typical Hand Cleaner Formulation | |
| --- | --- |
| Component | Total wt % |
| Mineral Spirits | 32% |
| Tall Oil Fatty Acid | 6% |
| Lanolin | 4% |
| Primary Alcohol Ethoxylate | 4% |
| Perfume | 0.1% |
| Propylene Glycol | 0.2% |
| White Oil | 2% |
| Aloe Vera | 0.2% |
| Water | 39% |
| Chelating Agent | 11% |
| Base - Caustic Soda | 0.6% |
| Preservative | 0.3% |
| Oil of Oregano | 0.6% |

In addition to antimicrobial hand cleaners, it is appreciated that the inventive natural essential oil active ingredients are operative in a variety of other consumer products in order to obtain reduced tendency towards antimicrobial resistance. These consumer products include bar soap, laundry soap, hand sanitizer, equipment cleaner, biological decontaminants, skin lotions, lubricants, moisturizer, deodorants, pine oil cleaning solutions, nasal spray, toothpaste, breath mints, and mouthwash. The inventive oil active ingredients are readily incorporated into such formulations by one skilled in the art.

Patents and publications mentioned in the specification are indicative of the level of skill in the art to which the invention pertains. These patents and publications are incorporated herein by reference to the same extent as if each individual patent or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

What is claimed is:

1. A waterless hand cleaner formulation comprising:
    an emulsifiable lipophilic organic solvent compatible with skin;
    a quantity of water present from 5 to 70 total weight percent;
    a surfactant system consisting of a nonionic surfactant and an optional at least one secondary HLB balancing catonic or anionic surfactant forming a gelatinous emulsion between said organic solvent and said quantity of water; and
    0.01 to 25 total weight percent of a natural essential oil comprising a complex solution of compounds derived from a plant varying in individual antimicrobial activity and having topical antimicrobial activity.

2. The formulation of claim 1 wherein said natural essential oil is present from 0.1 to 3 total weight percent.

3. The formulation of claim 1 wherein said natural essential oil is present from 0.3 to 1 total weight percent.

4. The formulation of claim 1 wherein said natural essential oil is selected from the group consisting of: anise, lemon, orange, oregano, rosemary, wintergreen, thyme, lavender, cloves, hops, tea tree, citronella, wheat, barley, lemongrass, cedar leaf cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradensis, Berberidaceae daceae, Ratanhiae* and *Curcuma longa*.

5. The waterless hand cleaner formulation of claim 1 wherein said natural essential oil is oil of oregano.

6. The formulation of claim 5 wherein, said oil of oregano is at least 60% by weight of carvacrol or a carvacrol derivative selected from a group consisting of carvacrol acetate, methyl carvacrol and cis dihydro carvone.

7. The formulation of claim 6 wherein said oil of oregano is fortified with carvacrol such that carvacrol and carvacrol derivatives comprise at least 80% by weight of said oil of oregano.

8. The formulation of claim 5 wherein said oil of oregano is present from 0.1 to 3 total weight percent.

9. The formulation of claim 1 further comprising at least one additional component selected from the group consisting of: emollient, fragrance, thixotropic agent, chelating agent, antioxidant and preservative.

10. An improved waterless hand cleaner formulation including an organic solvent, a quantity of water, a surfactant system forming an emulsion between said solvent and said quantity of water, said the surfactant system present in an amount to yield a gelatinous composition wherein the improvement lies in: 0.01 to 25 total weight percent of the formulation is a natural essential oil comprising a complex solution of compounds derived from a plant varying in individual antimicrobial activity and having topical antimicrobial activity and 5 to 70 total weight percent of the formulation is water and said surfactant system consist of a nonionic surfactant and an optional at least one secondary HLB balancing, cationic or anionic surfactant.

11. The improved formulation of claim 10 wherein the natural essential oil is selected from a group consisting of: anise, lemon, orange, oregano, rosemary. wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fix, balsam, menthol, ocmea origanum, *Hydastis carradensis, Berberidaceae daceae, Ratanhiae* and *Curcuma longa*.

12. The improved formulation of claim 10 wherein said natural essential oil is oil of oregano.

13. A process for cleaning and sanitizing a skin surface comprising the steps of:
    applying a gelatinous waterless hand cleaner formulation containing a surfactant system consisting of a nonionic surfactant and an optional at least one secondary HLB balancing, cationic or anionic surfactat, 5 to 70 total weight percent water, and 0.01 to 25 total weight percent of a natural essential oil, said natural essential oil comprising a complex solution of compounds derived from a plant varying in individual antimicrobial activity and having topical antimicrobial activity to the skin surface;
    allowing said formulation to remain in contact with the skin surface for an amount of time sufficient to yield a clean skin surface; and
    removing said formulation from the clean skin surface through water rinsing or wiping.

14. The process of claim 13 wherein said natural essential oil is present from 0.1 to 3 total weight percent.

15. The process of claim 13 wherein said natural essential oil is oil of oregano.

16. The process of claim 15 wherein said oil of oregano is at least 60% by weight of carvacrol or a carvacrol derivative selected from a group consisting of carvacrol acetate, methyl carvacrol and cis dihydro carvone.

17. The process of claim 16 wherein said oil of oregano is fortified with carvacrol such that carvacrol and carvacrol derivatives comprise at least 80% by weight of said oil of oregano.

18. The process of claim 15 wherein said oil of oregano is present from 0.1 to 3 total weight percent.

19. The formulation of claim 1 further comprising a thickener.

20. The formulation of claim 19 wherein said thickener is a hydroxy alkyl cellulose.

21. The improved formulation of claim 10 wherein the further improvement lies in: decreasing the amount of said organic solvent commensurate with the total weight percent of said natural essential oil.

22. The improved formulation of claim 10 wherein the further improvement lies in: increasing the amount of surfactant by 0.01 to 0.5 times the total weight percent of said natural essential oil.

* * * * *